(12) United States Patent
Thies et al.

(10) Patent No.: US 12,383,284 B2
(45) Date of Patent: Aug. 12, 2025

(54) METHOD AND APPARATUS FOR EFFECTING OSTEOCHONDRAL RESTORATION

(71) Applicant: Allosource, Centennial, CO (US)

(72) Inventors: Brendan Thies, Woodstock, GA (US); Justin Sluder, Marietta, GA (US); Leigh Anne Boros, Marietta, GA (US); Stephen Wilson Braun, Marietta, GA (US)

(73) Assignee: Allosource, Centennial, CO (US)

( * ) Notice: Subject to any disclaimer, the term of this patent is extended or adjusted under 35 U.S.C. 154(b) by 0 days.

(21) Appl. No.: 18/724,131

(22) PCT Filed: Feb. 27, 2024

(86) PCT No.: PCT/US2024/017379
§ 371 (c)(1),
(2) Date: Jun. 25, 2024

(87) PCT Pub. No.: WO2024/182332
PCT Pub. Date: Sep. 6, 2024

(65) Prior Publication Data
US 2024/0415527 A1   Dec. 19, 2024

Related U.S. Application Data

(60) Provisional application No. 63/448,506, filed on Feb. 27, 2023.

(51) Int. Cl.
*A61B 17/16* (2006.01)
*A61B 90/00* (2016.01)

(52) U.S. Cl.
CPC ...... *A61B 17/1635* (2013.01); *A61B 17/1637* (2013.01); *A61B 17/1677* (2013.01); *A61B 2090/062* (2016.02)

(58) Field of Classification Search
CPC .................................................. A61B 17/1637
See application file for complete search history.

(56) References Cited

U.S. PATENT DOCUMENTS

| | | | |
|---|---|---|---|
| 2,850,007 | A | 9/1958 | Lingley |
| 3,577,979 | A | 5/1971 | Van Der Gaast |

(Continued)

FOREIGN PATENT DOCUMENTS

| | | | |
|---|---|---|---|
| CN | 208769902 U | 4/2019 | |
| CN | 113317841 B | 7/2022 | |

(Continued)

OTHER PUBLICATIONS

English Translation of the Abstract for DE102012207846A1—Nov. 14, 2013, 1 pp.

(Continued)

*Primary Examiner* — Zade Coley
(74) *Attorney, Agent, or Firm* — James A. Sheridan; Sheridan Law, LLC

(57) ABSTRACT

There is disclosed apparatus for effecting osteochondral restoration. In an embodiment, the apparatus includes a tube having a distal end, a proximal end and a lumen extending therebetween. A drill shaft is rotatably disposed in the lumen of the tube, the drill shaft comprising a distal end and a proximal end. At least one cutting blade is disposed at the distal end of the drill shaft. A coring housing extends from the distal end of the tube and disposed around the at least one cutting blade, the coring housing terminating in a distal cutting surface. Other embodiments are also disclosed.

17 Claims, 9 Drawing Sheets

(56) References Cited

U.S. PATENT DOCUMENTS

| | | | |
|---|---|---|---|
| 4,142,517 A | 3/1979 | Contreras et al. | |
| 4,649,918 A | 3/1987 | Pegg et al. | |
| 4,785,826 A | 11/1988 | Ward | |
| 4,838,282 A | 6/1989 | Strasser | |
| 5,324,300 A | 6/1994 | Elias et al. | |
| 5,341,816 A | 8/1994 | Allen | |
| 5,423,823 A | 6/1995 | Schmieding | |
| 5,919,196 A * | 7/1999 | Bobic | A61F 2/4618 606/88 |
| 5,921,987 A * | 7/1999 | Stone | A61F 2/30756 606/80 |
| 6,017,348 A | 1/2000 | Hart et al. | |
| 6,592,588 B1 | 7/2003 | Bobic et al. | |
| 7,993,347 B1 | 8/2011 | Michelson | |
| 8,152,808 B2 * | 4/2012 | Steiner | A61B 17/1675 606/79 |
| 8,460,297 B2 * | 6/2013 | Watlington | A61B 17/1688 606/80 |
| 10,779,960 B2 | 9/2020 | Wahl | |
| 11,185,339 B2 * | 11/2021 | Perez | A61F 2/28 |
| 11,224,445 B2 * | 1/2022 | Figallo | A61B 17/1637 |
| 11,376,051 B2 | 7/2022 | McDonnell | |
| 2006/0173476 A1 * | 8/2006 | Bradica | A61B 17/1635 606/179 |
| 2007/0093841 A1 | 4/2007 | Hoogland | |
| 2008/0215055 A1 * | 9/2008 | Stone | A61B 17/1615 606/80 |
| 2009/0209962 A1 * | 8/2009 | Jamali | A61F 2/4644 606/89 |
| 2009/0299371 A1 * | 12/2009 | Steiner | A61B 17/1675 606/87 |
| 2012/0053588 A1 * | 3/2012 | Lozier | A61B 17/1615 408/214 |
| 2017/0143351 A1 | 5/2017 | Devitre et al. | |
| 2019/0166827 A1 | 6/2019 | Rorick | |
| 2019/0254683 A1 * | 8/2019 | Figallo | A61B 17/1637 |
| 2019/0358042 A1 * | 11/2019 | Taylor | A61F 2/4225 |
| 2021/0128306 A1 * | 5/2021 | Taylor | A61F 2/30756 |
| 2021/0146007 A1 | 5/2021 | Sakthivel et al. | |
| 2022/0217971 A1 | 7/2022 | Bhumiratana et al. | |
| 2022/0226128 A1 | 7/2022 | Du et al. | |
| 2022/0257382 A1 | 8/2022 | Hermsen et al. | |
| 2022/0265284 A1 * | 8/2022 | Arramon | A61B 17/1757 |

FOREIGN PATENT DOCUMENTS

| | | |
|---|---|---|
| CN | 217853065 U | 11/2022 |
| DE | 102012207846 A1 | 11/2013 |
| FR | 2429007 A1 | 1/1980 |

OTHER PUBLICATIONS

English Translation of the Abstract for FR2429007—Jan. 18, 1980, 1 pp.
International Search Report and Written Opinion issued for Int. Appl. No. PCT/US2024/017379, Jun. 11, 2024, 11 pp.
English Translation of CN112217841, 6 pp.
English Translation of CN208789902, 6 pp.
English Translation of CN217853065, 5 pp.

* cited by examiner

METHOD AND APPARATUS FOR EFFECTING OSTEOCHONDRAL RESTORATION

FIELD OF THE INVENTION

This invention relates to medical devices for use in surgical applications in general, and more particularly to novel methods and apparatus for effecting osteochondral restoration.

BACKGROUND

Trauma and/or disease to articulating joints (e.g., the knee joint) can cause structural damage to the articular cartilage surface and the underlying subchondral bone, resulting in pain and/or disability for the patient. The area of the articular cartilage (and/or underlying subchondral bone) that is damaged is commonly referred to as a "lesion". Lesions may develop as the result of disease that affects the cartilage and/or bone or, perhaps more commonly, as the result of sporting injuries in which shear forces cause a separation of cartilage between the radial and calcified layers of bone. Chondral lesions lie entirely within the cartilage and do not penetrate into the subchondral bone. Osteochondral lesions penetrate the articular surface in depth, into the vascularized subchondral bone.

To treat an osteochondral lesion, a surgeon must remove the diseased/damaged cartilage together with a portion of the underlying bone. The resulting cavity is then filled with either a cellular graft, an osteochondral graft, or an allograft/autograft derived cartilage implant. For the purposes of the instant disclosure, the term "allograft" is intended to mean a donor derived or artificially derived (e.g., synthetic, lab-grown, etc.) tissue graft, and the term "autograft" is intended to mean a tissue graft obtained from the patient that is being treated (i.e., a tissue graft transferred from one area of the patient's body to the treatment site).

Currently, surgeons perform osteochondral restoration using a variety of different surgical instruments, often in concert with one another. By way of example, a surgical coring tool comprising a cylindrical thin-walled tube enclosing a lumen having a fixed cutting blade disposed perpendicular to the axis of the lumen may be used, with the surgeon manually rotating the coring tool in order to "core out" a plug of tissue and bone. Alternatively, a cannulated surgical drill bit configured to fit over a guidewire may be used in concert with an appropriate surgical drill in order to "drill out" a plug of tissue and bone. Alternatively, a ring curette and bone curette may be used to outline the lesion and another, smaller curette may be used to "remove" a plug of material outlined by the ring or bone curette.

It will be appreciated that each of these surgical methods and apparatus result in a time-consuming procedure requiring a variety of different tools which sometimes do not match the size/geometry of the lesion that is to be removed. Moreover, tools such as a manually-operated coring tool, a drill bit or a curette require significant skill on the part of the surgeon in order to remove the lesion and prepare a cavity of the proper depth and size to receive the graft.

Thus, there is a need for a new and improved method and apparatus for performing osteochondral restoration that combines the functions of various surgical instruments into a single device, which permits the surgeon to precisely locate and core circular sections of cartilage and bone to a precise depth so as to create a cavity for receiving a graft.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In various embodiments, there are provided method and apparatus for performing osteochondral restoration that combines the functions of various surgical instruments into a single device, and which permits the surgeon to precisely locate and core circular sections of cartilage and bone so as to create a cavity having a precise depth for receiving a graft.

In an embodiment, there is provided apparatus for effecting osteochondral restoration, the apparatus comprising a tube having a distal end, a proximal end and a lumen extending therebetween; a drill shaft rotatably disposed in the lumen of the tube, the drill shaft comprising a distal end and a proximal end; at least one cutting blade disposed at the distal end of the drill shaft; and a coring housing extending from the distal end of the tube and disposed around the at least one cutting blade, the coring housing terminating in a distal cutting surface.

In another embodiment, there is provided a method for effecting osteochondral restoration, the method comprising providing apparatus comprising a tube having a distal end, a proximal end and a lumen extending therebetween; a drill shaft rotatably disposed in the lumen of the tube, the drill shaft comprising a distal end and a proximal end; at least one cutting blade disposed at the distal end of the drill shaft; and a coring housing extending from the distal end of the tube and disposed around the at least one cutting blade, the coring housing terminating in a distal cutting surface; placing the distal cutting surface over a lesion that is to be removed such that the lesion is bounded by the coring housing; applying a distally-directed force to the distal cutting surface such that the cutting surface cuts into the tissue around the perimeter of the lesion; and moving the drill shaft distally and rotating the drill shaft such that the at least one cutting blade cuts into the tissue bounded by the coring housing, whereby to core out a cavity in the tissue comprising the lesion.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
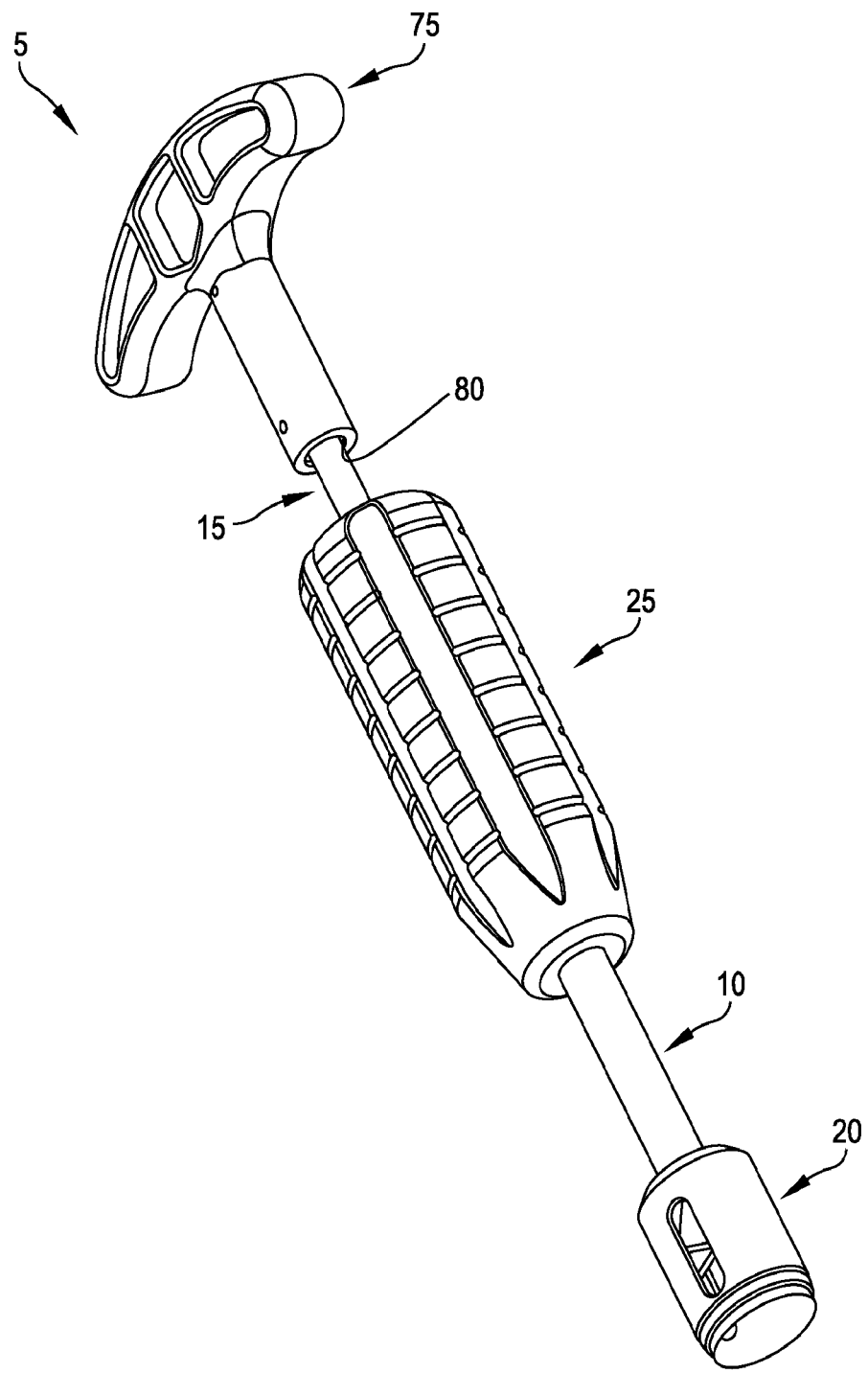
FIGS. 1-3 are schematic views showing a novel surgical coring apparatus formed in accordance with the present invention.
Figure 2:
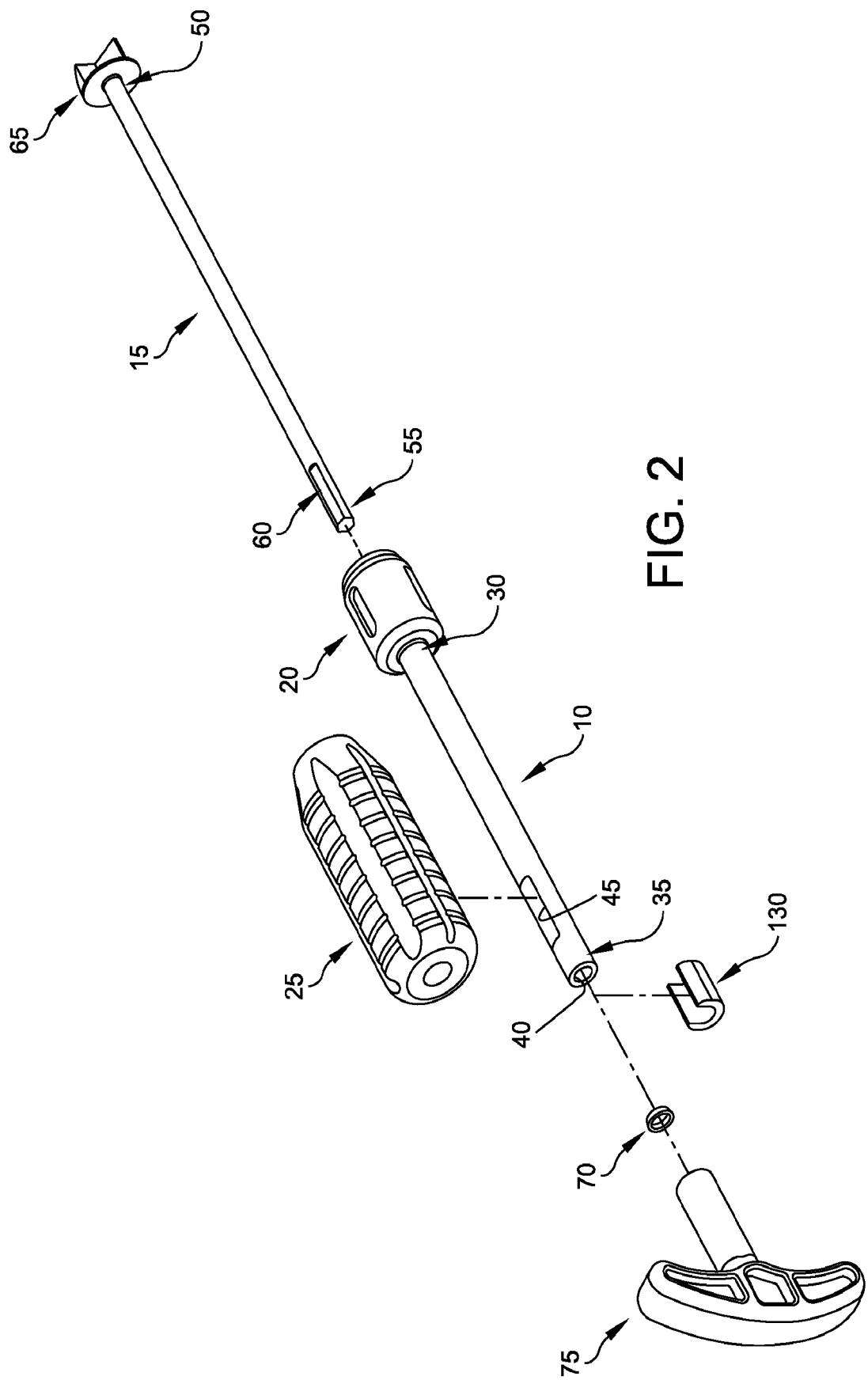
Figure 3:
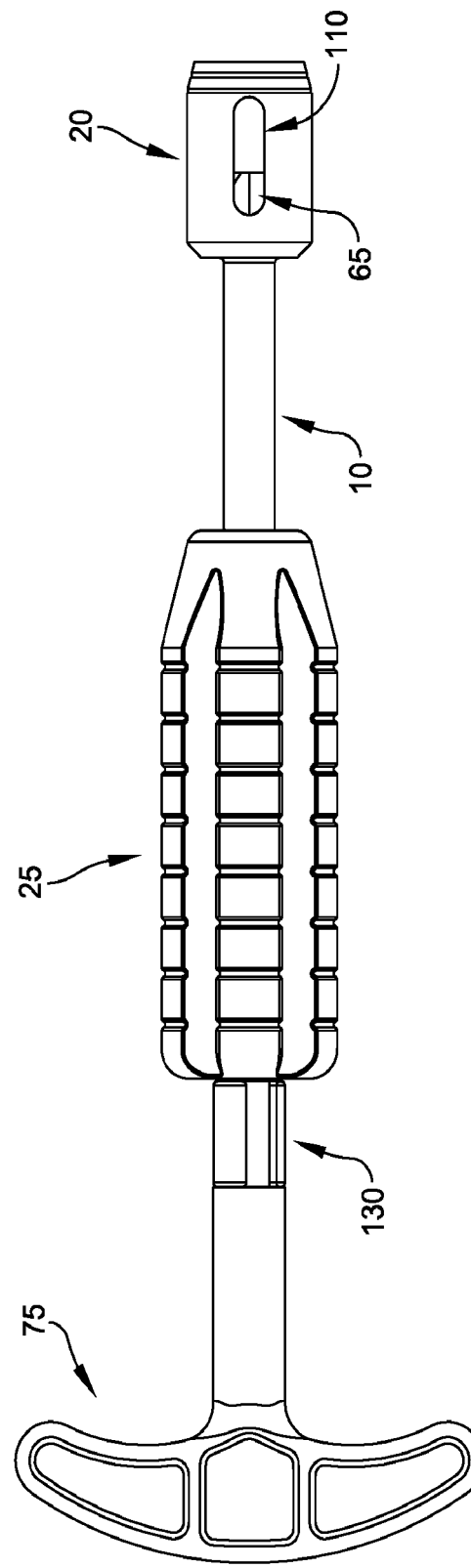
Figure 4:
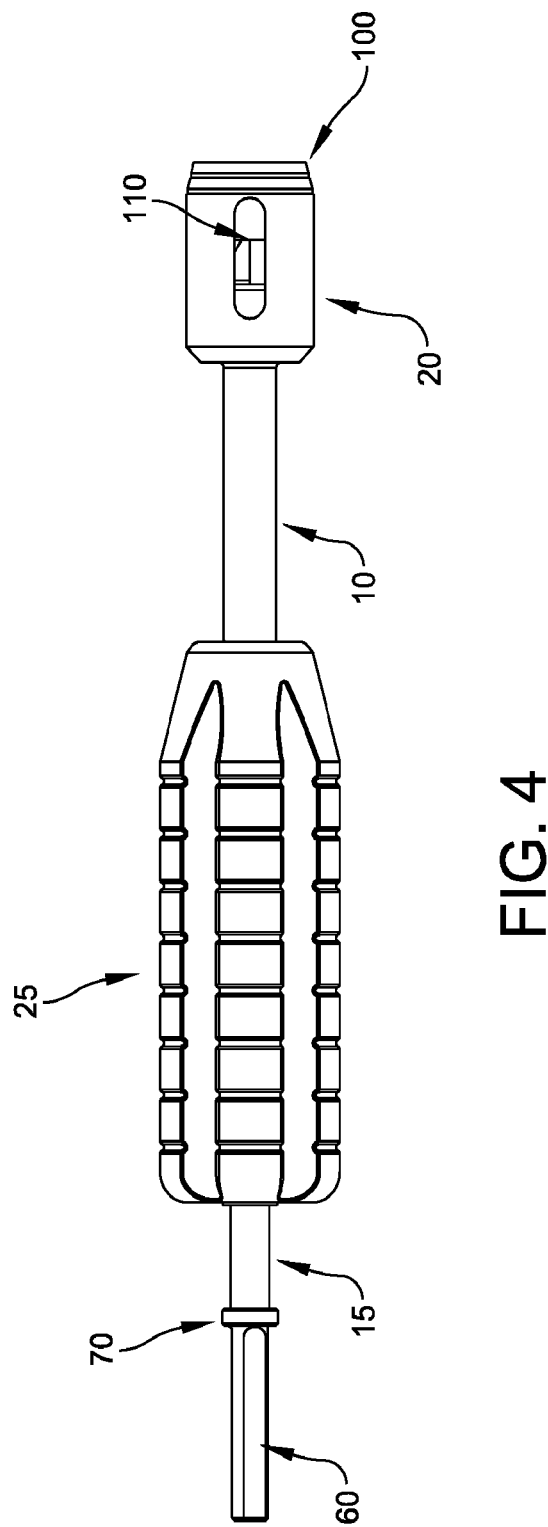
FIGS. 4 and 5 are schematic views showing the novel surgical coring apparatus of FIGS. 1-3 with the handle omitted.
Figure 5:
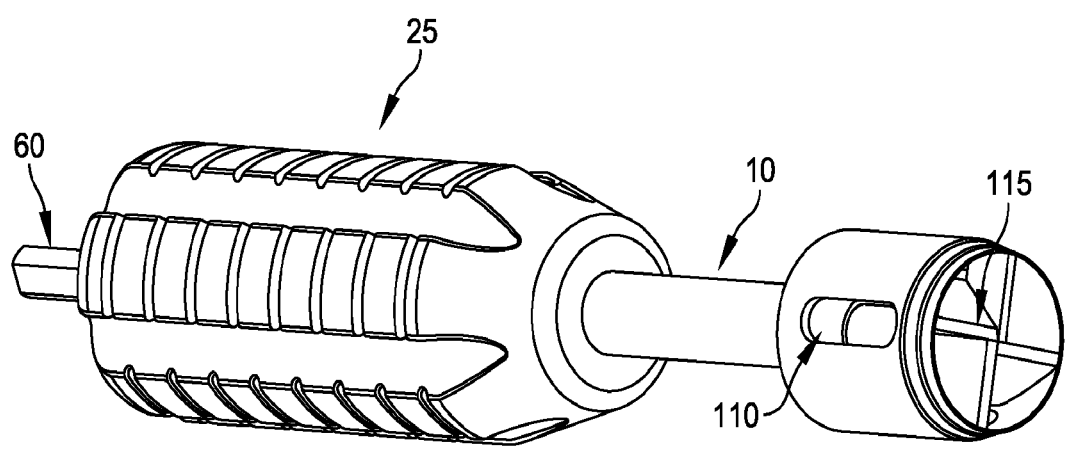

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

In various embodiments, there may be provided a new and improved method and apparatus for performing osteochondral restoration that combines the functions of various surgical instruments into a single device, and which permits the surgeon to precisely locate and core circular sections of cartilage and bone so as to create a cavity having a precise depth for receiving a graft.

Looking now at FIGS. 1-5, there is shown a novel surgical coring apparatus 5 formed in accordance with the present invention. Apparatus 5 generally comprises a tube 10, a drill shaft 15, a coring housing 20, and an over grip 25 disposed over a portion of tube 10, as will hereinafter be discussed in further detail.

More particularly, and still looking at FIGS. 1-5, tube 10 comprises a distal end 30, a proximal end 35, and a lumen 40 extending therebetween. Lumen 40 of tube 10 is sized to slidably and rotatably receive drill shaft 15 therein such that drill shaft 15 can move longitudinally relative to tube 10 and/or rotate relative to tube 10, as will hereinafter be discussed. If desired, one or more windows 45 may be formed in the sidewall of tube 10 intermediate distal end 30 and proximal end 35 in order to communicate with lumen 40, whereby to facilitate mounting of over grip 25 to tube 10 and/or to facilitate passing an irrigation fluid or vacuum through tube 10, as will hereinafter be discussed in further detail.

Drill shaft 15 comprises a distal end 50 and a proximal end 55. Proximal end 55 of drill shaft 15 comprises at least one flat 60 extending distally along a portion of drill shaft 15 for mounting a handle to proximal end 55 of drill shaft 15, as will hereinafter be discussed in further detail. A drill bit 65 is mounted to, or formed integral with, distal end 50 of drill shaft 15, as will hereinafter be discussed in further detail. A radially-extending stop 70 (FIG. 2) is mounted at a selected point along drill shaft 15 so as to prevent drill bit 65 from moving beyond the distal end of coring housing 20, as will hereinafter be discussed in further detail.

A handle 75 is preferably mounted to proximal end 55 of drill shaft 15, whereby to permit manual movement (either longitudinal movement or rotational movement) of drill shaft 15 relative to tube 10. Handle 75 comprises a recess 80 (FIG. 1) having at least one groove (not shown) configured to mate with flat 60 formed on proximal end 55 of drill shaft 15, whereby to secure handle 75 to drill shaft 15 via a press fit. In one preferred form of the invention, drill shaft 15 comprises three flats 60 formed at proximal end 55, whereby to present a triangular cross-section which is received in a complementary triangular-shaped recess 80 formed in handle 75. As a result of this construction, manual movement (either longitudinal movement or rotational movement) of handle 75 causes corresponding longitudinal and/or rotational movement of drill shaft 15 (and hence of drill bit 65 mounted to distal end 50 of drill shaft 15).

Figure 6:
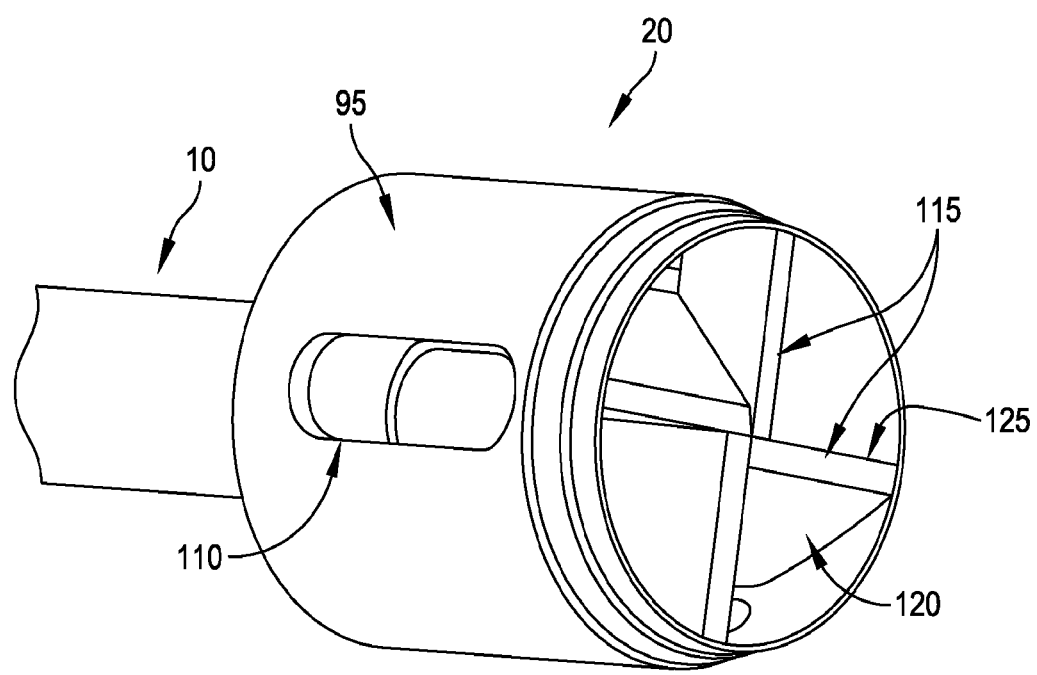
FIGS. 6-8 are schematic views showing further aspects of the distal end of the novel surgical coring apparatus of FIGS. 1-3.
Figure 7:
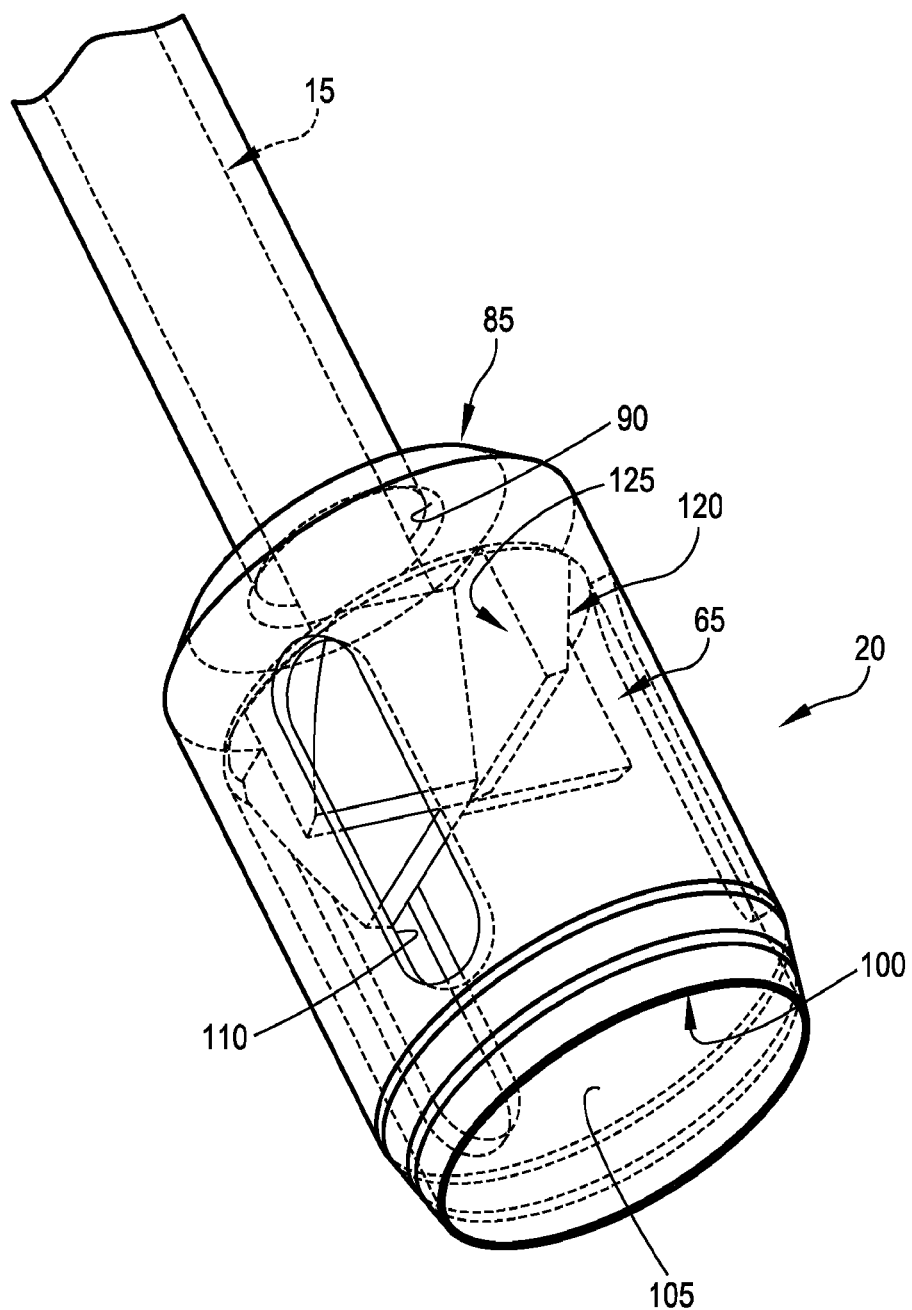
Figure 8:
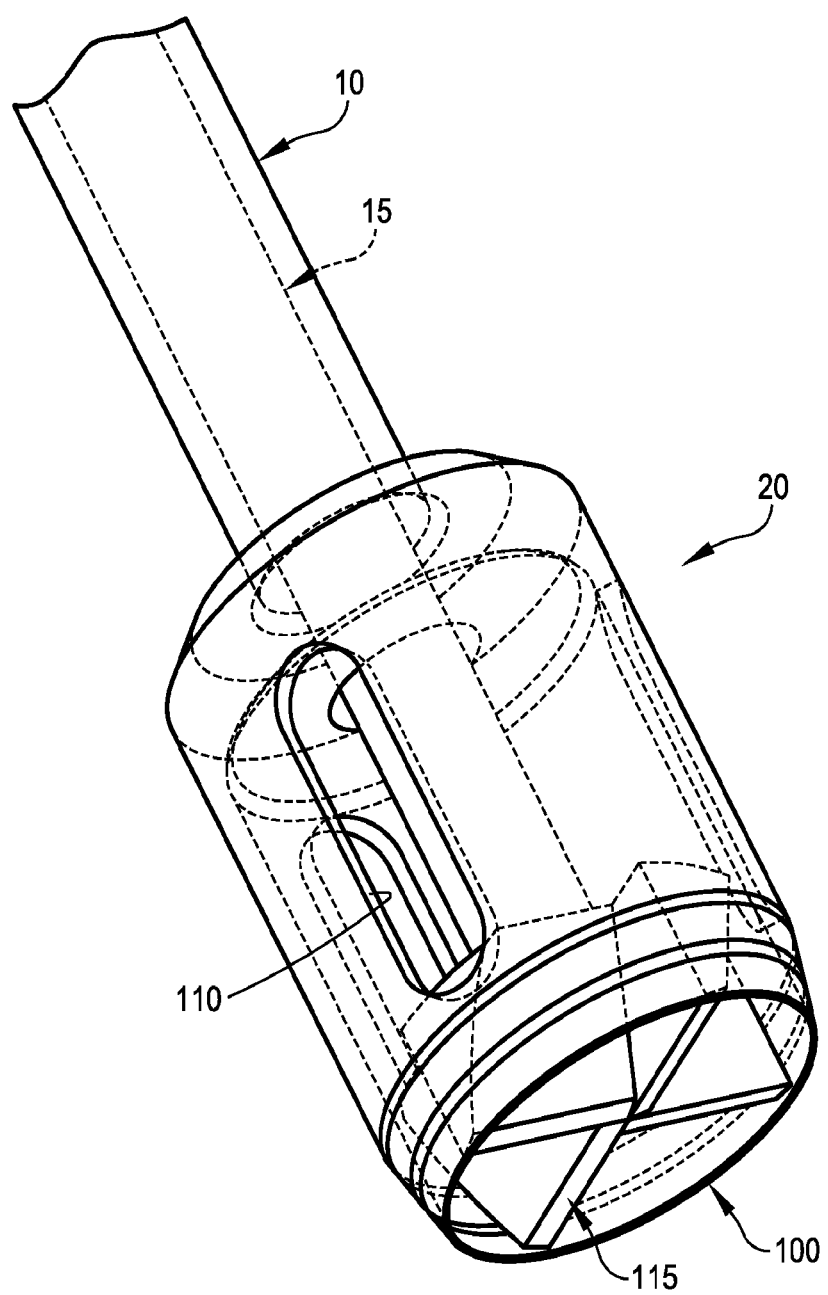
Figure 9:
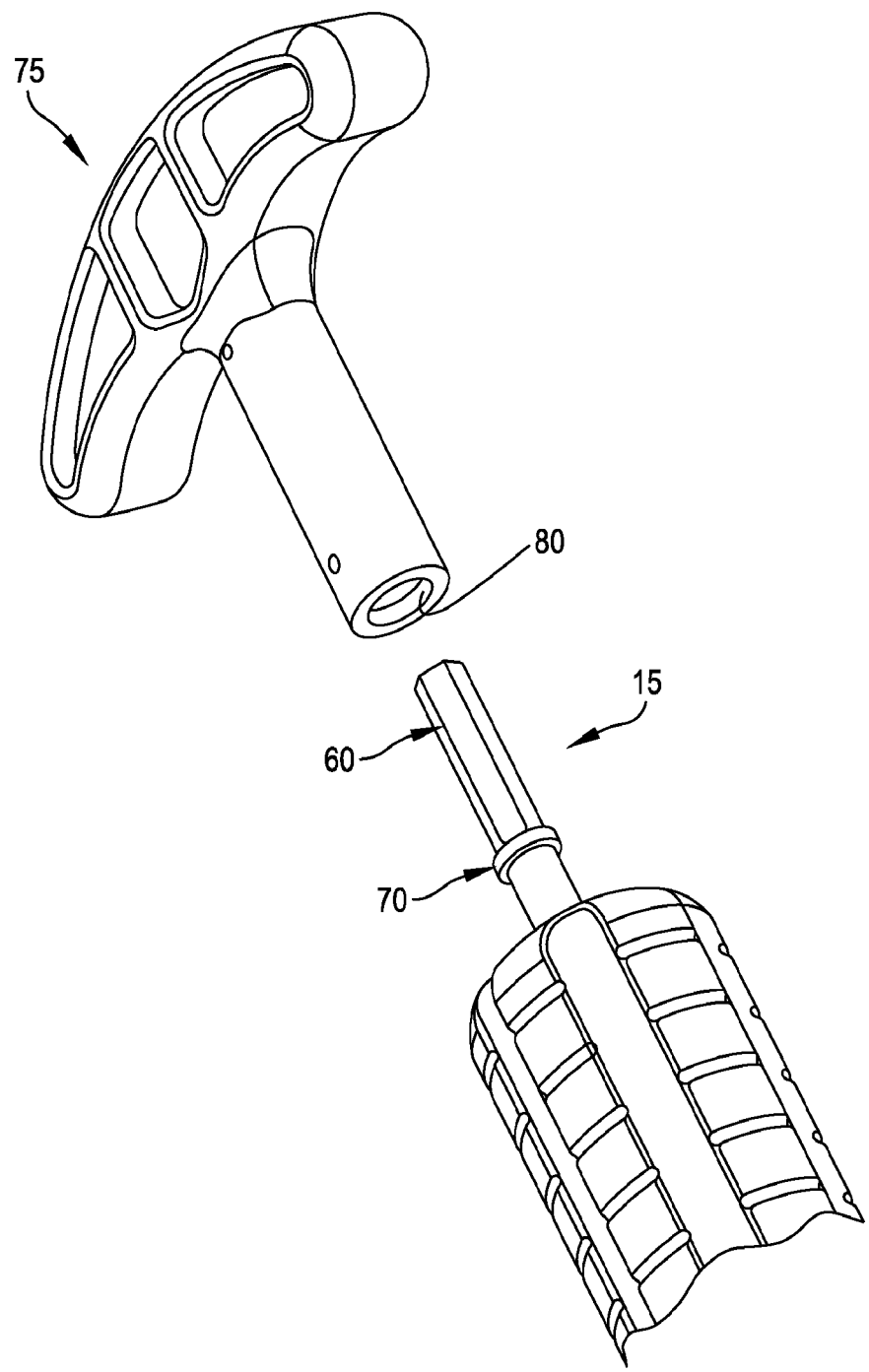
FIG. 9 is a schematic view showing further aspects of the proximal end of the novel surgical coring apparatus of FIGS. 1-3.

Looking now at FIGS. 6-8, coring housing 20 comprises a proximal baseplate 85 mounted to (or formed integral with) distal end 30 of tube 10. Baseplate 85 comprises an opening 90 (FIG. 7) sized to permit drill shaft 15 to pass therethrough. A circumferentially-extending sidewall 95 is mounted to baseplate 85 and extends distally therefrom, terminating in a distal cutting surface 100. Sidewall 95 extends circumferentially about the perimeter of baseplate 85 and defines a cavity 105 sized to receive drill bit 65 therein, as will hereinafter be discussed in further detail. One or more windows 110 are preferably formed in sidewall 95 so as to communicate with cavity 105, whereby to permit irrigation fluid and/or vacuum to be introduced into cavity 105 and/or to facilitate removal of a plug of tissue from cavity 105, as will hereinafter be discussed in further detail.

Still looking at FIGS. 6-8, drill bit 65 preferably comprises a plurality of cutting blades 115. Cutting blades 115 each comprise a front cutting surface 120 disposed at an angle relative to the longitudinal axis of drill shaft 15, and a rear surface 125 disposed generally parallel to the longitudinal axis of drill shaft 15. In one preferred form of the invention, drill bit 65 comprises four cutting blades 115, with the cutting blades 115 arranged such that the front cutting surface 120 of each cutting blade 115 is configured to cut tissue when drill bit 65 is rotated in a first (e.g., clockwise) direction relative to the tissue to be cored out. It will be appreciated that, as a result of the angle of front cutting surface 120 of each cutting blade 115, as tissue is cut by the cutting blade 115, the tissue removed is directed proximally back behind drill bit 65, whereby to enter cavity 105 of coring housing 20, whereupon the cut tissue can be expelled (or actively removed, e.g., via a vacuum) through the one or more windows 110 formed in sidewall 95, as will hereinafter be discussed in further detail.

In one preferred form of the present invention, a removable spacer 130 is releasably mounted to proximal end 55 of drill shaft 15 so as to prevent longitudinal movement of drill shaft 15. More particularly, and looking now at FIG. 3, in a preferred form of the invention, spacer 130 is releasably mounted to proximal end 55 of drill shaft 15 so as to be captured between the distal end of handle 75 (or stop 70 of drill shaft 15) and the proximal end of over grip 25, whereby to prevent handle 75 (and hence, drill shaft 15 mounted thereto) from moving distally until spacer 130 is removed from drill shaft 15.

It will also be appreciated that drill shaft 15 is sized such that, when spacer 130 is removed, drill bit 65 mounted to distal end 50 of drill shaft 15 can be moved distally and proximally within cavity 105 of coring housing 20. To this end, stop 70 on drill shaft 15 is configured to contact over grip 25 when drill shaft 15 is in its distalmost position, whereby to prevent further distal movement of drill shaft 15. In this way, cutting blades 115 of drill bit 65 will never extend distally beyond distal cutting surface 100 of sidewall 95 when drill shaft 15 is in its distalmost position.

It should also be appreciated that, if desired, the outer surface of sidewall 95 of coring housing 20 may comprise indicia (not shown), e.g., a series of regularly spaced depth markings, to provide a visual reference to the surgeon for how far distal cutting surface 100 is advanced into tissue.

Exemplary Use of Surgical Coring Apparatus 5 to Effect Osteochondral Reconstruction In use, when a surgeon wishes to effect an osteochondral reconstruction using novel apparatus 5 of the present invention, the surgeon selects an apparatus 5 comprising a coring housing 20 sized and shaped to fit over a lesion that is to be removed. To this end, it should be appreciated that coring housing 20 is preferably provided in different geometries (e.g., oval, square, rectangular, etc.) and different sizes (e.g., so as to define a cavity 105 of different dimensions) so as to be sized and shaped for the lesion that is to be removed.

Once the surgeon has selected an appropriately configured apparatus 5 to remove the lesion, the surgeon accesses the lesion that is to be removed (e.g., via an incision, a cannula, etc.) and moves apparatus 5 such that coring housing 20 is disposed over the lesion that is to be removed. With spacer 130 mounted to drill shaft 15, the surgeon applies a distally-directed force to handle 75. Since spacer 130 prevents distal movement of drill shaft 15, the distally-directed force moves coring housing 20 distally such that distal cutting surface 100 of sidewall 95 engages and cuts into the tissue around the perimeter of the lesion that is to be removed. The surgeon may rotate apparatus 5 (e.g., by rotating over grip 25) so as to help facilitate the cutting action of distal cutting surface 100. If provided on the outer surface of sidewall 95, the surgeon can use indicia markings (not shown) to determine how far distal cutting surface 100 has advanced into the tissue that is to be cored, whereby to determine when distal cutting surface 100 is disposed distally at the desired depth.

Once distal cutting surface 100 has been inserted distally into the tissue to the correct depth, the surgeon removes spacer 130 and moves handle 75 distally, whereby to move drill shaft 15 (and hence, drill bit 65 mounted thereto) distally so as to engage and cut tissue within cavity 105 of coring housing. Once drill bit 65 has been moved distally a distance sufficient to engage tissue disposed within cavity 105 of coring housing 20, the surgeon rotates handle 75, whereby to rotate drill shaft 15 and drill bit 65. As drill bit 65 rotates in a first direction (e.g., a clockwise direction), cutting blades 115 engage and cut tissue, with tissue being directed up along front cutting surface 120 into the area behind drill bit 65. From this point, tissue can be removed by removing apparatus 5 from the body of the patient (carrying the tissue cored out within cavity 105) where it is thereafter removed from cavity 105, e.g., via prying it out using windows 110 to gain access or by applying a vacuum to suction the cored tissue from within cavity 105.

This results in a "plug" of tissue being cored out of the tissue, leaving a recess in the tissue having the shape of cavity 105 and extending from the surface of the tissue to the depth at which distal cutting surface 100 is disposed during cutting. Since the size and geometry of the recess cored out of the tissue matches the size and geometry of cavity 105 (as modified by the depth to which distal cutting surface 100 extends into the tissue), and since apparatus 5 is selected by the surgeon so as to precisely match the cellular graft, an osteochondral graft, or an allograft/autograft that is to be inserted into the recess that is formed, apparatus 5 provides a simple way to accurately form a recess in tissue that can receive the cellular graft, osteochondral graft, or allograft/autograft with which the surgeon wishes to repair the tissue. The cellular graft, osteochondral graft, or allograft/autograft is then inserted into the recess cored into the tissue and the osteochondral reconstruction procedure is complete.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method for effecting osteochondral restoration, the method comprising:
   providing apparatus comprising:
      a tube having a distal end, a proximal end and a lumen extending therebetween;
      a drill shaft rotatably disposed in the lumen of the tube, the drill shaft comprising a distal end and a proximal end;
      at least one cutting blade disposed at the distal end of the drill shaft; and
      a coring housing extending from the distal end of the tube and disposed around the at least one cutting blade, the coring housing terminating in a distal cutting surface;
   placing the distal cutting surface over a lesion that is to be removed such that the lesion is bounded by the coring housing;
   applying a distally-directed force to the distal cutting surface such that the cutting surface cuts into the tissue around the perimeter of the lesion; and
   without removing the distal cutting surface from the tissue around the perimeter of the lesion, moving the drill shaft distally and rotating the drill shaft such that the at least one cutting blade cuts into the tissue bounded by the coring housing, whereby to core out a cavity in the tissue comprising the lesion;
   wherein the apparatus further comprises a spacer removably mounted to the proximal end of the drill shaft with:
      a first configuration in which the spacer mounted to the drill shaft prevent the drill shaft from moving in a distal direction through the tube, and
      a second configuration in which the spacer removed from the drill shaft allows the drill shaft to move in the distal direction through the tube, and
   wherein the method further comprises providing the spacer mounted to the proximal end of the drill to prevent the drill shaft from moving in the distal direction through the tube during the step of applying the distally-directed force to the distal cutting surface such that the cutting surface cuts into the tissue around the perimeter of the lesion.

2. The method of claim 1, wherein the at least one cutting blade comprises a front cutting surface disposed at an angle relative to a longitudinal axis of the drill shaft, and a rear surface disposed generally parallel to the longitudinal axis of the drill shaft.

3. The method of claim 1, further comprising removing the spacer from the drill prior to moving the drill shaft distally to allow the drill shaft to move in the distal direction through the tube during the step of moving the drill shaft distally and rotating the drill shaft such that the at least one cutting blade cuts into the tissue bounded by the coring housing, whereby to core out a cavity in the tissue comprising the lesion.

4. The method of claim 1, wherein the step of applying a distally-directed force to the distal cutting surface such that the cutting surface cuts into the tissue around the perimeter of the lesion includes cutting the tissue comprising both cartilage and bone.

5. The method of claim 1, wherein the step of applying a distally-directed force to the distal cutting surface such that the cutting surface cuts into the tissue around the perimeter of the lesion includes cutting the tissue comprising a depth of cartilage through to bone without cutting into the bone.

6. The method of claim 1, wherein the step of applying a distally-directed force to the distal cutting surface such that the cutting surface cuts into the tissue around the perimeter of the lesion includes cutting the tissue comprising a depth of cartilage without cutting through the cartilage to bone.

7. The method of claim 1, wherein the apparatus further comprises a radially-extending stop mounted at a selected point along the drill shaft in a configuration to prevent the at least one cutting blade from moving beyond the distal cutting surface of the coring housing, and wherein the method further comprises (1) advancing the distal cutting surface to a given depth in the tissue during the step of applying the distally-directed force to the distal cutting surface, and (2) coring out the cavity in the tissue proximal of, or to, the given depth of the distal cutting surface as limited by the radially-extending stop.

8. A method for effecting osteochondral restoration, the method comprising:
providing apparatus comprising:
a tube having a distal end, a proximal end and a lumen extending therebetween;
a drill shaft rotatably disposed in the lumen of the tube, the drill shaft comprising a distal end and a proximal end;
at least one cutting blade disposed at the distal end of the drill shaft;
a coring housing extending from the distal end of the tube and disposed around the at least one cutting blade, the coring housing terminating in a distal cutting surface; and
a radially-extending stop mounted at a selected point along the drill shaft in a configuration to prevent the at least one cutting blade from moving beyond the distal cutting surface of the coring housing;
placing the distal cutting surface over a lesion that is to be removed such that the lesion is bounded by the coring housing;
applying a distally-directed force to the distal cutting surface such that the cutting surface cuts into the tissue around the perimeter of the lesion; and
moving the drill shaft distally and rotating the drill shaft such that the at least one cutting blade cuts into the tissue bounded by the coring housing, without moving beyond the distal cutting surface of the coring housing as prevented by the radially-extending stop, whereby to core out a cavity in the tissue comprising the lesion;
wherein the apparatus further comprises a spacer removably mounted to the proximal end of the drill shaft with:
a first configuration in which the spacer mounted to the drill shaft prevent the drill shaft from moving in a distal direction through the tube, and
a second configuration in which the spacer removed from the drill shaft allows the drill shaft to move in the distal direction through the tube, and
wherein the method further comprises providing the spacer mounted to the proximal end of the drill to prevent the drill shaft from moving in the distal direction through the tube during the step of applying the distally-directed force to the distal cutting surface such that the cutting surface cuts into the tissue around the perimeter of the lesion.

9. The method of claim 8, further comprising removing the spacer from the drill prior to moving the drill shaft distally to allow the drill shaft to move in the distal direction through the tube during the step of moving the drill shaft distally and rotating the drill shaft such that the at least one cutting blade cuts into the tissue bounded by the coring housing, whereby to core out a cavity in the tissue comprising the lesion.

10. The method of claim 8, wherein the step of applying a distally-directed force to the distal cutting surface such that the cutting surface cuts into the tissue around the perimeter of the lesion includes cutting the tissue comprising both cartilage and bone.

11. The method of claim 8, wherein the step of applying a distally-directed force to the distal cutting surface such that the cutting surface cuts into the tissue around the perimeter of the lesion includes cutting the tissue comprising a depth of cartilage through to bone without cutting into the bone.

12. The method of claim 8, wherein the step of applying a distally-directed force to the distal cutting surface such that the cutting surface cuts into the tissue around the perimeter of the lesion includes cutting the tissue comprising a depth of cartilage without cutting through the cartilage to bone.

13. A method for effecting osteochondral restoration, the method comprising:
providing apparatus comprising:
a tube having a distal end, a proximal end and a lumen extending therebetween;
a drill shaft rotatably disposed in the lumen of the tube, the drill shaft comprising a distal end and a proximal end;
at least one cutting blade disposed at the distal end of the drill shaft;
a coring housing extending from the distal end of the tube and disposed around the at least one cutting blade, the coring housing terminating in a distal cutting surface; and
a radially-extending stop mounted at a selected point along the drill shaft in a configuration to prevent the at least one cutting blade from moving beyond the distal cutting surface of the coring housing;
placing the distal cutting surface over a lesion that is to be removed such that the lesion is bounded by the coring housing;
applying a distally-directed force to the distal cutting surface to advance the distal cutting surface by cutting into the tissue around the perimeter of the lesion to a given depth in tissue surrounding the perimeter of the lesion; and
without removing the distal cutting surface from the tissue around the perimeter of the lesion, moving the drill shaft distally and rotating the drill shaft such that the at least one cutting blade cuts into the tissue bounded by the coring housing, whereby to core out a cavity in the tissue comprising the lesion proximal of, or to, the given depth of the distal cutting surface as limited by the radially-extending stop;
wherein the apparatus further comprises a spacer removably mounted to the proximal end of the drill shaft with:
a first configuration in which the spacer mounted to the drill shaft prevent the drill shaft from moving in a distal direction through the tube, and a second configuration in which the spacer removed from the drill shaft allows the drill shaft to move in the distal direction through the tube, and wherein the method further comprises providing the spacer mounted to the proximal end of the drill to prevent the drill shaft from moving in the distal direction through the tube during the step of applying the distally-directed force to the distal cutting surface such that the cutting surface cuts into the tissue around the perimeter of the lesion.

14. The method of claim 13, further comprising removing the spacer from the drill prior to moving the drill shaft distally to allow the drill shaft to move in the distal direction through the tube during the step of moving the drill shaft distally and rotating the drill shaft such that the at least one cutting blade cuts into the tissue bounded by the coring housing, whereby to core out a cavity in the tissue comprising the lesion.

15. The method of claim 13, wherein the step of applying a distally-directed force to the distal cutting surface such that the cutting surface cuts into the tissue around the perimeter of the lesion includes cutting the tissue comprising both cartilage and bone.

16. The method of claim 13, wherein the step of applying a distally-directed force to the distal cutting surface such that the cutting surface cuts into the tissue around the perimeter of the lesion includes cutting the tissue comprising a depth of cartilage through to bone without cutting into the bone.

17. The method of claim 13, wherein the step of applying a distally-directed force to the distal cutting surface such that the cutting surface cuts into the tissue around the perimeter of the lesion includes cutting the tissue comprising a depth of cartilage without cutting through the cartilage to bone.

* * * * *